United States Patent [19]

Goble et al.

[11] Patent Number: 4,870,957
[45] Date of Patent: Oct. 3, 1989

[54] LIGAMENT ANCHOR SYSTEM

[76] Inventors: E. Marlowe Goble, 850 E. 1200 North; W. Karl Somers, 651 N. 150 West, both of Logan, Utah 84321

[21] Appl. No.: 289,728

[22] Filed: Dec. 27, 1988

[51] Int. Cl.[4] ............................................. A61F 5/04
[52] U.S. Cl. ................................. 128/92 YF; 623/13
[58] Field of Search ................ 128/69, 92 R, 92 YE, 128/92 YF, 92 YJ; 623/12, 13; 24/453, 623, 625, 694

[56] References Cited

U.S. PATENT DOCUMENTS

| | | | |
|---|---|---|---|
| 3,973,277 | 8/1976 | Semple et al. | 128/92 YF |
| 4,301,551 | 11/1981 | Dore et al. | 623/13 |
| 4,640,271 | 2/1987 | Lower | 128/92 YF |
| 4,694,544 | 9/1987 | Chapman | 24/625 |
| 4,760,843 | 8/1988 | Fischer et al. | 128/92 YF |
| 4,772,286 | 9/1988 | Goble et al. | 623/13 |

FOREIGN PATENT DOCUMENTS 3630390  3/1987  Fed. Rep. of Germany ........ 623/13

Primary Examiner—Robert A. Hafer
Assistant Examiner—Charles H. Sam
Attorney, Agent, or Firm—M. Reid Russell

[57] ABSTRACT

An anchor system that is preferably for use in an arthoscopic cruciate ligament replacement procedure for securing a ligament (37) or (50), or ligament type device, with or without a stint (38), within a prepared ligament tunnel (33). The system includes a pair of threaded footings (11) for turning in opposite tapped ligament tunnel cortex ends (34) and (35) and studs (10), each having an eyelet end (18) or, for a prosthetic ligament (50) is secured to the ligament end, the studs each having a cylindrical body (17) and flared end (12). The stud flared end terminates in a lip (15) wherefrom a lock wall (16) extends at an angle to the vertical to the cylindrical body, which flared end is cross-cut at (19) and (20), forming sections. The stud flared end (12) sections to close together to fit through the threaded footing (11) and flex outwardly beyond that footing end (24), the lip lock wall (16) to flex over that footing end locking the stud therein.

In practice, the ligament (37) with or without the stint (38) is formed into a loop for sliding along the stud (10), slot (20) into the eyelet (18), or the studs are attached to a prosthetic ligament ends in its manufacture, the pair of studs and connected ligament and stint for manipulation through an arthoscopic port (36) formed into the patient's knee, each stud for seating into a threaded footing, the studs each locking therein with the ligament stretched across the knee intra articular joint. Whereafter, tension on the ligament can be adjusted by individually turning the threaded footings appropriately into or out of the cortex threads.

23 Claims, 4 Drawing Sheets

LIGAMENT ANCHOR SYSTEM

BACKGROUND OF THE INVENTION

1. Field of the Invention

This invention relates to ligament anchor systems and devices for use in an arthoscopic surgical procedure and particularly relates to repair or replacement of a knee cruciate ligament.

2. Prior Art

In the discipline of arthoscopic knee surgery, for a particular procedure, a surgeon will form a tunnel through the tibia, intra articular joint, and femur, that is to receive an anterior or posterior cruciate ligament maintained therein. Such ligament ends can be attached, as with staples, to the femoral and/or tibial cortex surface, maintaining the ligament, under tension, across the intra articular joint. Examples of arrangements for attaching ligaments to the tibial and femoral cortexes are shown in a United Kingdom Patent, No. G.B. 2,084,468A and a patent of the present inventors, U.S. Pat. No. 4,772,286. Also a U.S. patent application, Ser. No. 246,324, of the present inventors entitled "Apparatus and Procedure for Verifying Isometric Ligament Positioning", filed Sept. 19, 1988, teaches that a ligament end can be secured to a threaded sleeve, the sleeve for turning in threads formed in a femoral or tibial cortex.

Neither the above cited United Kingdom patent, nor the earlier patent and patent application of the present inventors, however, includes a pair of longitudinally open threaded footings for turning in tunnel cortex ends and for receiving ligament mounting studs fitted therein, as does the present invention. Further, unlike earlier ligament attachment arrangements, the present invention provides for both placing a ligament and/or stint in tension between the studs, across the intra articular joint, and provides for adjusting the tension at either the femoral or tibial cortex tunnel ends.

SUMMARY OF THE INVENTION

It is a principal object of the present invention to provide, for use in a knee arthoscopic surgical procedure, a ligament anchor system for securing a biological or prosthetic ligament, or ligament type device, with or without a stint, as a replacement for an anterior or posterior cruciate ligament.

Another object of the present invention is to provide an arrangement for securing a ligament, ligament type device, with or without a stint, within a prepared cruciate ligament tunnel that is formed through the patient's femur, intra articular joint and tibia, where the installation is completed through an arthoscopic port into the knee, and with the final ligament tensioning adjusted at the femoral or tibial cortex tunnel end or ends.

Another object of the present invention is to provide a system where, after healing, tension on an installed ligament, ligament type device, with or without a stint, can be released at either the tibial or femoral cortex ends of the ligament tunnel.

Another object of the present invention is to provide as end couplings, a pair of studs for mounting a ligament, or ligament type device therebetween, with or without a stint, each stud for individual coupling in one of a pair of threaded footings that are individually turned into the respective femoral and tibial cortex tunnel ends, the studs to turn freely within the threaded footings.

Still another object of the present invention is to provide a ligament and stint mounting that is easily installed during a knee arthoscopic surgical procedure that includes studs wherebetween the ligament is maintained that are individually mounted and dismounted into threaded footings that are turned into the opposite tunnel ends, with final tension adjustments to be made by turning the respective threaded footings into or out of the femoral and tibial cortex tunnel ends.

Still another object of the present invention is to provide a system of pairs of studs and threaded footings where, with an increasing tensile force applied through a stud that is seated in a footing, the footing threads will tend to flex outwardly into the threads of a tapped cortex tunnel end purchasing additional holding strength.

Still another object of the present invention is to provide a ligament anchor system that may be biodegradable for mounting a ligament, or ligament type device, with or without a stint, within a prepared cruciate ligament tunnel, and for releasing that mounting after healing.

The present invention is in a ligament anchor system that includes a pair of studs wherebetween a biological ligament, or the like, is to be positioned, each stud having an outwardly flared end terminating in a lip. The stud flared end is essentially pie shaped to slope rearwardly towards a closed eyelet stud end and includes a cylindrical shaft therebetween. The stud flared end is cross-cut into the cylindrical shaft, which cuts are at approximately ninety (90) degree increments to each other. The one pair of cuts to align with the stud eyelet end, and the other pair aligned to bisect the eyelet end open portion. Which bisecting pair of cuts are preferably continued into that eyelet open portion. An open passage is thereby formed from the stud cross-cut flared end into the eyelet to allow free passage of a ligament, string, or the like, fitted therethrough. For a prosthetic, the studs, less the eyelet ends, are secured, as in the manufacture to the prosthetic ligament ends.

The pair of studs are to fit individually in externally threaded footings. The threaded footings are essentially sleeves and are turned in a tapped ligament tunnel end cortex. The stud, at its flared end section, will flex inwardly at the cross-cuts when passed through the threaded footing. The stud flared end, after that passage, to flex or spring outwardly when it travels beyond the threaded footing end. The stud includes a flared end lip that will extend beyond, to overlap, the threaded footing end. Each threaded footing, for an anterior cruciate ligament replacement procedure, is arranged for turning in a tapped end of a ligament tunnel. Which tunnel, for an anterior cruciate ligament, extends from the femoral anterolateral cortex, across the intra articular joint, to the tibial cortex at the tibial tuberosity. The threads of each threaded footing are sloped appropriately to "bite" or "slide", at each thread flight into the tapped cortex threads so as to further lock the footing in that cortex when a tensile force is applied as would tend to pull the stud out from the footing.

The longitudinal passage through each threaded footing is internally walled at one end, as with a hexagonal cross-section, to receive a driver fitted therein for turning it into the tapped cortex. Further, opposite external slots may be formed longitudinally in the footing, to a depth just below the threads and proximate to one end, for receiving flat tabs or ears of a straddle tool that are fitted therein for turning the seated footing. The straddle tool flat tabs or ears are identical and have a thickness that is less than the footing thread height so as to allow the footing to be turned freely into or out of the tapped cortex.

In practice, for a biological ligament, the footings are individually turned, utilizing a driver, an appropriate distance into the respective femur and tibia cortexes and the distance between the opposite footing ends is determined. An appropriate length of ligament or ligament type device, with or without a stint, or a stint alone, is then formed into a continuous loop and is fitted or strung through and between the pair of stud eyelets. With the knee flexed appropriately, the total distance between the stud flared end lips should be approximately equal to the spacing distance between the opposite footing ends.

The linked studs can be fitted through an arthoscopic port formed into the knee and each stud is manipulated to fit through one of the threaded footings. The one stud is fitted through the ligament tunnel and is set into a first threaded footing, and the second stud is maintained within the knee while the second threaded footing is turned into the cortex. Thereafter, the second stud can be manipulated by a surgeon operating through the arthoscopic port, who slides the stud into the second threaded footing, stretching the ligament, with or without stint, therebetween. Tension is then tested by moving the knee and, if an adjustment is needed, one or both of the footings can be turned further into or out of their respective cortex seats from without the knee, utilizing the straddle tool.

If it is desired to release tension on the ligament and/or stint, after the bone growth has anchored the ligament, a small incision can be made into the knee, to expose an end of the ligament tunnel, so as to provide access to the stud flared end. Which stud flared end, below the lip, can then be cut, allowing the stud to slide within the footing, releasing tension on the ligament and/or stint.

BRIEF DESCRIPTION OF THE DRAWINGS

These and other objects and features of the present invention will become more apparent from the following description in which the invention is described in detail in conjunction with the accompanying drawings.

DETAILED DESCRIPTION

Figure 1:
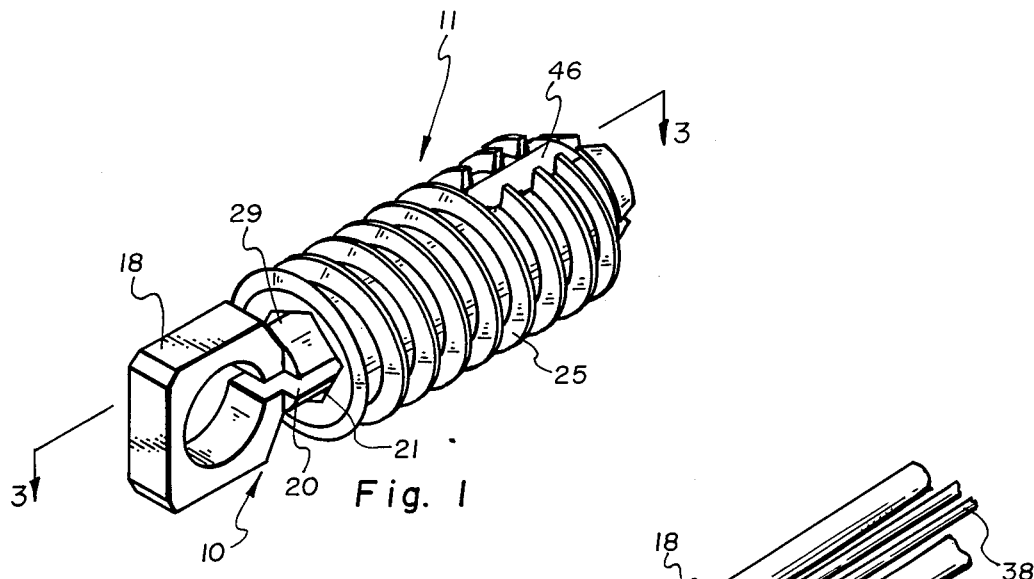
FIG. 1 is a profile perspective view of a cross-cut stud and threaded footing of the invention shown joined together as a ligament anchor.

In FIG. 1 is shown a profile perspective view of the present invention in a cross-cut stud 10 fitted into a threaded footing 11 shown as a cylindrical sleeve that is externally threaded along its length and is open through a center longitudinal passage. As will be set out hereinbelow, the cross-cut stud is locked in the threaded footing when slid fully through the longitudinal passage.

Figure 2:
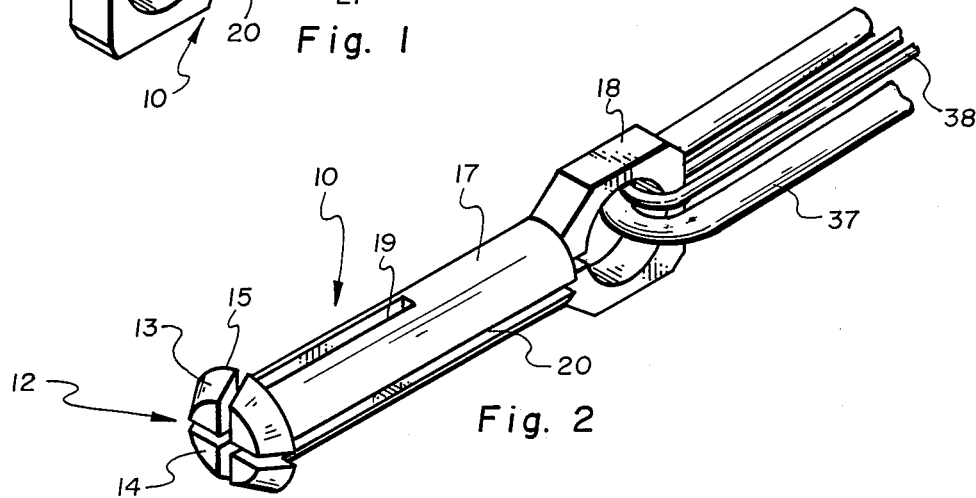
FIG. 2 is a profile perspective view of the stud of FIG. 1 removed from a threaded footing of the ligament anchor, with a biological ligament and stint shown arranged through an eyelet end of the stud.

FIG. 2 shows the cross-cut stud 10, hereinafter referred to as stud, as including a flared end 12, that is essentially pie shaped, and has a sloping wall 13 that tapers outwardly from a flat nose 14, terminating in a rounded circumferential lip 15, as shown best in FIGS. 2 and 3, a lock wall 16, slopes inwardly to intersect the forward end of a stud cylindrical body 17. A rearmost end of which cylindrical body 17 connects to a stud eyelet 18 end. Which eyelet 18 is shown as a center holed narrow rectangular section secured at one end to extend axially from the cylindrical body.

The stud 10 is preferably formed as a single unit from a material that is suitable for human implantation, either metal or plastic, and is selected to be somewhat resilient. The stud is cross-cut along a vertical plane at 19 and a horizontal plane at 20, as shown best in FIG. 2. The horizontal cut 20 preferably extends from the flared end 12, through the cylindrical body 17, and into eyelet 18. The vertical cut 19 extends from the flared end 12 to approximately a mid-point of the cylindrical body 17. So arranged, the resiliency of stud 10 allows the cylindrical body segments formed from flared end 12 along cross-cuts 19 and 20 to bend inwardly towards one another. The diameter of the flared end lip 15 can thereby be reduced to less than the diameter of a longitudinal passage 21 that is formed through the threaded footing 11. Accordingly, to install the stud 10 in a threaded footing 11, as shown in FIG. 3, the stud flared end sloping wall 13 is fitted into a threaded footing at its outwardly flared end 22, and is urged therein. In that passage, the stud flared end and cylindrical body segments are closed together at the cross-cuts 19 and 20, allowing that stud flared end to pass into and slide along and through that threaded footing longitudinal passage 21.

Figure 3:
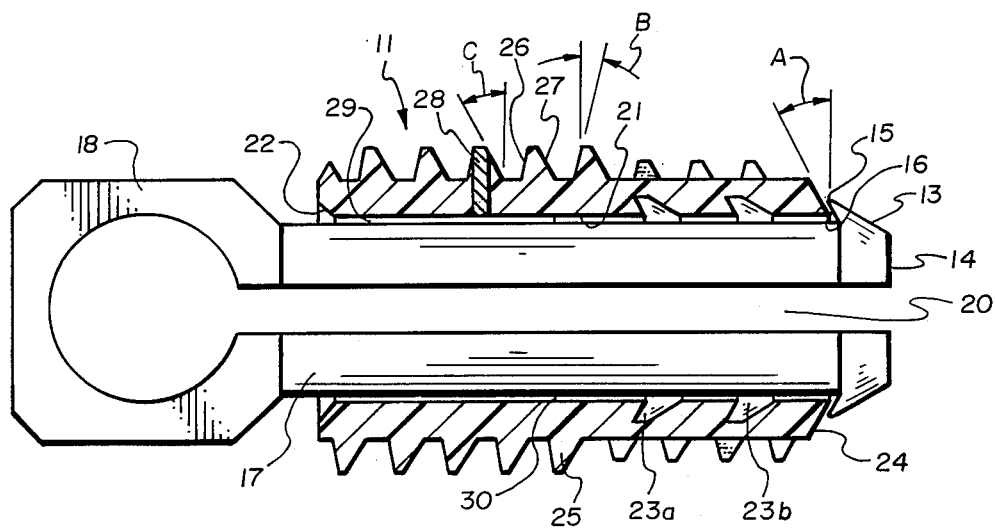
FIG. 3 is a side elevation sectional view taken along the line 3—3 of FIG. 1, showing with arrows, the preferred thread angles relative to the vertical of the forward and rear face and footing nose.

In stud 10 passage along the threaded footing 11, as shown in FIG. 3, the stud flared end 12 will intersect and expand into intermediate first and second flared grooves, 23a and 23b, respectively, that may be formed around the longitudinal passage 21 wall. Intermediate grooves 23a and 23b are similarly formed, each to have forward and rearwardly facing walls that are slanted from the vertical to approximately the same angles as the stud flared end sloping and lock walls, 13 and 16, respectively. So arranged, on alignment of the stud flared end 12 with a first or second flared groove 23a or 23b, that stud flared end will expand into that flared groove, the stud flared end lock wall 16 coming to rest on the flared groove rearwardly facing wall, prohibiting stud 10 withdrawal. With a continued application of force on stud 10, at eyelet 18 end, the stud flared end sloping wall 13 will slide over the flared groove forward wall, the stud flared end and cylindrical body segments flexing inwardly, towards one another, and allowing the stud to continue through the threaded footing. Of course, a threaded footing 11 without the first and second intermediate grooves 23a and 23b, can be utilized within the scope of this disclosure when it is desirable to provide for releasing the stud from the threaded footing so as to adjust a ligament or stint length. Accordingly, it should be understood, a threaded footing 11 with or without the first and second flared grooves 23a and 23b will come within the scope of this disclosure.

Shown in FIG. 3, the stud flared end 12 has passed beyond a threaded footing sloping end 24, and the lock wall 16 has moved outwardly over that footing sloping end, the stud flared end segments having flexed outwardly. The stud 10 is thereby seated in threaded footing 11. This seating will be maintained against an application of a tensile force on the stud 10 at eyelet 18. In such force application the angular configuration to the vertical of the stud lock wall 16 and threaded footing end 24 is such that the stud lock wall 16 will be urged outwardly along the threaded footing end 24, purchasing additional holding strength. Shown at arrow A in FIG. 3, an angle of approximately thirty (30) degrees from the vertical has been selected for forming stud lock wall 16 and threaded foot end 24. In practice, it is believed that an angle in a range from ten (10) to sixty (60) degrees will work satisfactorily for this application.

For a threaded footing 11 fabricated from a resilient plastic material, as shown in the cross-sectional view of FIG. 3, such as Delrin TM, an increased tensile stress exerted on stud 10 will act through that stud to compress the threaded footing. In such force application the threaded footing threads 25 tend to expand outwardly. In such outward expansion, the threads are seated deeper into the threads tapped into a bone cortex, further purchasing tension holding strength. A preferred threaded footing 11 is formed to have a forward sloping face 27, shown as angle C in FIG. 3, to the vertical of approximately thirty (30) degrees and a rearward sloping face 26 of approximately twelve (12) degrees to the vertical, shown as angle B. In practice, it is believed, a threaded footing thread forward sloping face 27 of from twenty (20) to forty-five (45) degrees to the vertical, and a rearward sloping face 26 of from zero (0) to thirty (30) degrees to the vertical will function successfully for this application.

For a threaded footing 11, as shown in FIG. 3, a tensile force applied at eyelet 18 of stud 10 will tend to compress the footing, urging the threads 25 further into a tapped cortex, purchasing additional holding or pull out strength. It should, however, be understood that the threaded footing 11 and even the stud 10, need not necessarily be manufactured from a plastic material, such as Delrin TM, for this to occur. Threaded footing 11, can be manufactured from any surgically acceptable material, including a metal such as titanium, within the scope of this disclosure. However, where a plastic material is used, a metal marker 28 is preferably included therein as an x-ray marker.

Figure 4:
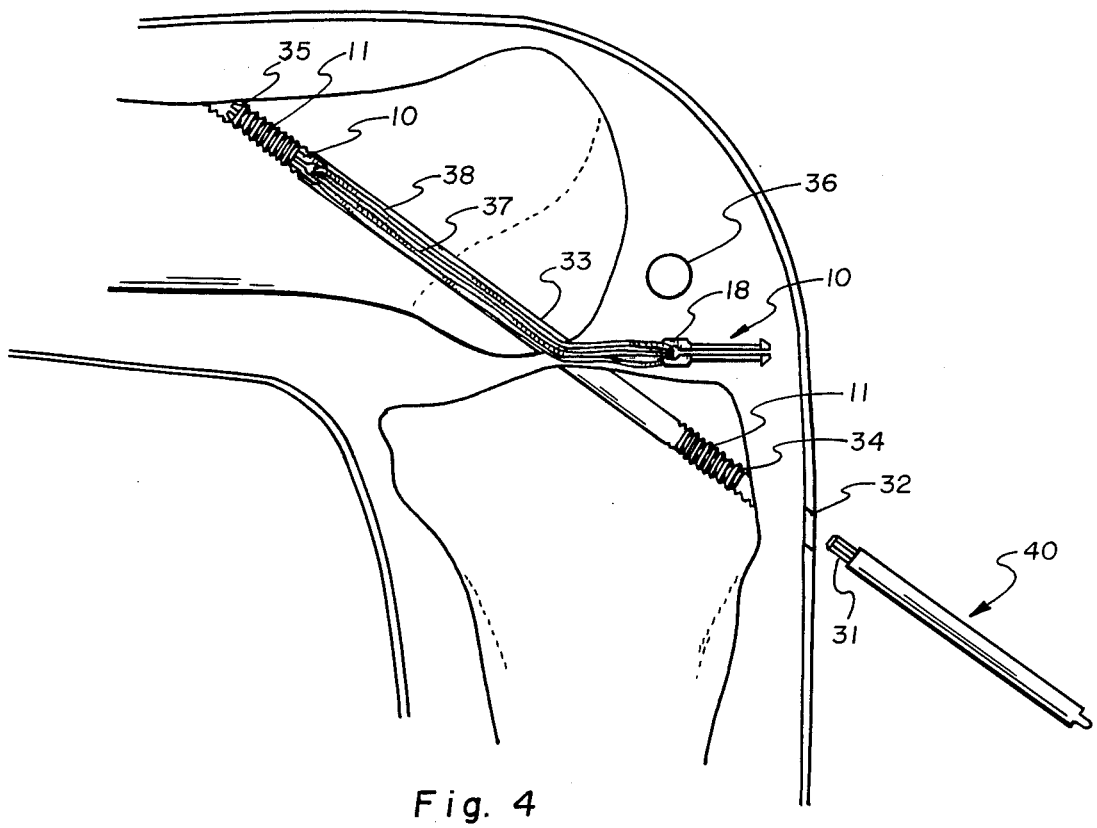
FIG. 4 is a side elevation view of a patient's knee with skin covering thereover and wherein an anterior cruciate ligament tunnel has been formed and the femoral and tibial cortex ends tapped and showing the threaded footing with a first cross-cut stud of FIG. 1 turned in the femoral cortex tunnel end, a ligament and stint extending therefrom and from a second cross-cut stud that is located within the knee and showing a driver aligned with the tibial cortex end of the ligament tunnel.

For turning the threaded footing 11 into a tapped cortex, as shown in FIGS. 1, 3 and 4, the threaded footing longitudinal passage 21 is preferably walled appropriately at one end 29 to receive a compatible sided driver end fitted therein. Shown best in FIGS. 3 and 4, the threaded footing walled end 29 is preferably formed to have a hexagonal cross-section that extends along the longitudinal passage to approximately a midpoint, shown at 30. Whereat, the longitudinal passage changes to a smooth circular cross-section from walled passage end 30 to its sloping end 24. The diameter of which longitudinal passage smooth portion is such as to accommodate the sided end 31 of a driver 40 that is fitted therein to engage the longitudinal passage walled portion 29 for turning the threaded footing.

Figure 6:
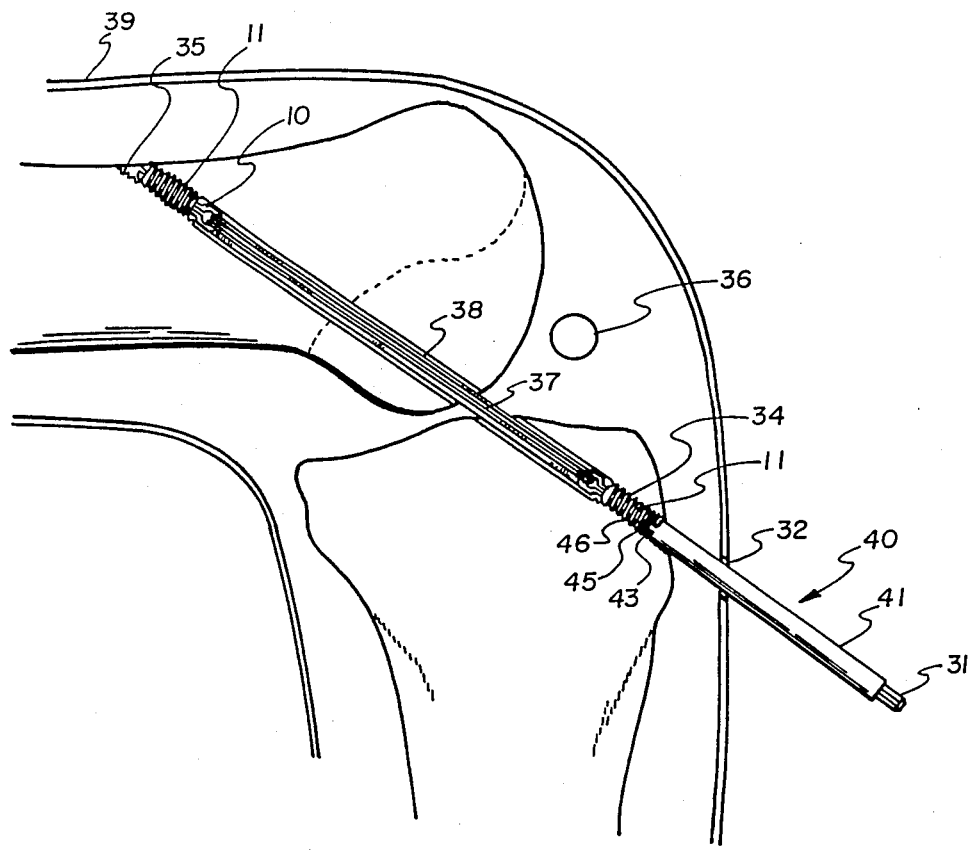
FIG. 6 is a view like that of FIG. 5 showing a straddle tool end of the driver end of the driver fitted through the tibial tunnel end and fitted to turn the threaded footing into or out of the tapped cortex.
Figure 7:
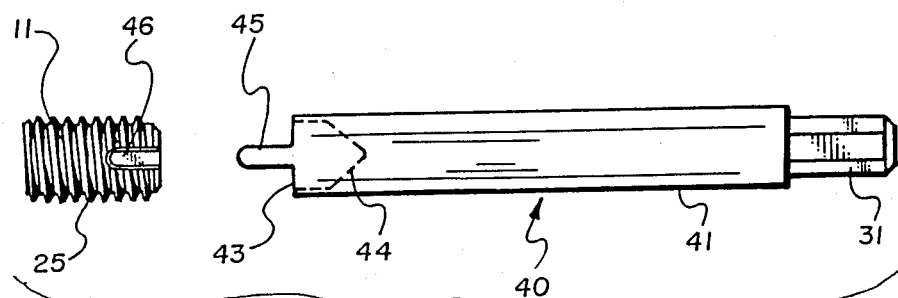
FIG. 7 is an enlarged view of the threaded footing and driver with straddle tool end of FIG. 6 aligned therewith.

Shown in FIGS. 4, 6 and 7, the driver 40 preferably includes a hexagonal headed end 31, that is aligned for fitting through a tibial incision 32 to travel through the threaded footing smooth portion and into the walled portion of the longitudinal passage 21. The driver hexagonal headed end for turning that threaded footing into or out of threads 34 that are tapped into the tibial cortex end of a ligament tunnel 33.

FIG. 4 also shows another threaded footing 11 that has been turned into threads 35 tapped into the femoral cortex end of the ligament tunnel 33. A stud 10 is shown fitted in the femoral cortex threaded footing 11 wherefrom a ligament 37 and stint 38 extend from the stud eyelet 18. The ligament 37 and stint 38 are shown to be continuous loops and are individually fitted through each eyelet ends 18 of a pair of studs 10. The ligament 37 and stint 38 and a stud 10 are shown in FIG. 4 positioned within the patient's knee. In practice, the ligament and stint can be slid along the stud horizontal cut 20, from the stud flared end 12 to stud eyelet 18, as illustrated in FIG. 3.

As shown in FIG. 4, one stud 10 is fitted into locking engagement within the threaded footing 11 that is turned into the femoral cortex threads 35. This seating can be accomplished prior to the turning of the second threaded footing 11 into the tibial cortex threads 34. Or, both studs 10 may be seated in threaded footings 11 by a surgeon manipulating each stud 10 through an arthoscopic port 36 formed in the patient's knee.

Figure 5:
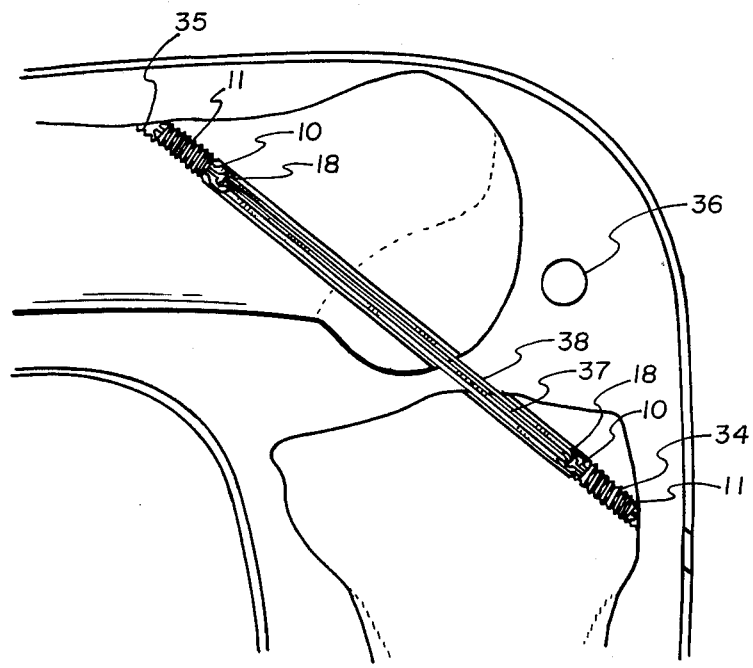
FIG. 5 is a view like that of FIG. 4, showing the pair of threaded footings seated in the femoral and tibial tunnel ends and showing first and second cross-cut studs fitted therein, and the ligament and stint stretched therebetween across the intra articular joint.

With the patient's leg maintained, as shown in FIGS. 4 through 6, and the threaded footings 11 seated in the tibial and femoral cortex threads 34 and 35, respectively, the length of the ligament 37 and stint 38 can be calculated based on the distance between the ends 22 of the threaded footings 11 taking into account the lengths of the pair of studs 10 to their lock walls 16. The ligament and stint are shown arranged as continuous loops and are fitted through the eyelets 18 of the pair of studs 10. The one stud 10 of the pair of studs, as shown in FIG. 4, is fitted into the threaded footing 11 that has been turned into threads 35 at the femoral cortex. Though, of course, a stud 10 may be first fitted into the threads 34 at the tibial cortex. The second stud 10, is then manipulated within the knee by a surgeon through the arthoscopic port 36, fitting it into the second threaded footing 11 that has been turned into the tibial cortex ligament tunnel end and stretching the ligament 37 and stint 38 therebetween, as shown in FIG. 5.

Preferably, as shown in FIG. 5, the ligament 37 and stint 38 are maintained between the pair of studs eyelet 18 seated in threaded footings 11 will be under a desired tensile stress. If that stress is materially different than an optimum stress for the procedure, one or both of the studs 10 can be released from their seating, and the studs pulled therefrom allowing a surgeon to reform the ligament and stint loops to new lengths. To provide such release, one or both of the stud flare ends 12 are compressed manually, or with a tool, not shown. The stud lip 15 diameter is thereby appropriately reduced so as to allow it to be pulled back through the threaded footing longitudinal passage 21. Of course, if a threaded footing with flared grooves 23a and 23b like that shown in FIG. 3, is in place, it will be required to provide for stud release within that threaded footing by compressing together the flared end segments to be maintained along the longitudinal until the first flared groove 23a is passed.

After the studs 10 have been seated in the threaded footings 11, as shown in FIG. 5, should it be determined that fine adjustments to the ligament and stint length are required, such can be made, as shown in FIG. 6, by turning one or both threaded footings 11 into or out of the respective femoral and tibial cortexes. This turning is preferably provided utilizing a straddle tool end 43 of driver 40. The straddle tool end 43 is for manual insertion and manipulation through a tibial or femoral ligament tunnel incision 32 or 39, respectively, as shown FIG. 6. As show best in FIG. 7, the driver 40 is preferably a solid rod 41 with the hexagonal sided end 31 that, as set out above, is for turning the threaded sleeves 11 into a tapped cortex, and includes the straddle tool 43 on its opposite end. Of course, the driver body can be formed from a tube within the scope of this disclosure.

Figure 8:
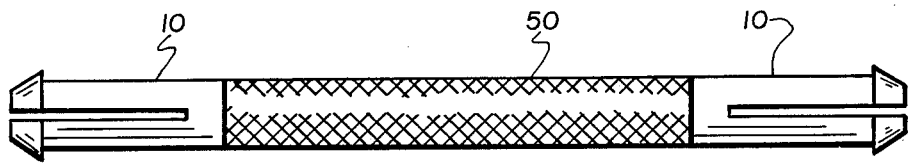
FIG. 8 is a side elevation view of a prosthetic ligament having studs like that shown in FIG. 2 secured to its opposite ends.

In FIG. 7, the driver straddle tool end 43 is shown to include a concave depression 44 formed longitudinally therein, shown in broken lines, that is to receive a threaded footing end and stud flared end nested therein. The driver straddle tool end 43 further includes at least a pair of tabs or ears 45 that extend from opposite points longitudinally outwardly. Which tabs or ears 45 are to fit into slots 46 that are formed from the footing end into the threads 25 of the threaded footing 11. The tabs or ears 45 preferably have a thickness such that, when fitted into the slots 46, their outer surfaces will be below the apex of threads 25. So arranged, as shown in FIG. 6, the straddle tool end 43 of driver 40 can be fitted through a tibial or femoral incision, the tabs or ears 45 traveling below the threads tapped into the femoral or tibial cortex and fitting into the slots 46 that are formed in the threaded footing end 24. So arranged, the threaded footing 11 can be turned further into or out of the tapped cortex, thereby adjusting the tensioning on the ligament and stint.

Where a ligament 37 and stint 38 have been shown as being utilized together, it should be understood that either can be used alone or another linkage, such as a tendon, can be used instead of, or therewith, within the scope of this disclosure. Also, after healing, if it is desired to release the tension on such ligament and/or stint, this can easily be accomplished at a femoral or tibial incision. In such procedure the incision is opened to expose a stud flared end 12, which end is then cut thereacross, releasing that flared end, such that the remainder of the stud 10 will travel back through the threaded footing 11.

Where the pair of studs 10 are shown as separate units from ligament 37 and stint 38, it should be understood that for a prosthetic ligament 50, like that shown in FIG. 8, the stud 10, less the eyelet end 18 can be secured, preferably in the manufacturing process, extend axially from the prosthetic ligament 50 ends. So arranged, functioning of the prosthetic ligament 50 having stud 10 ends for installation in threaded footings 11 would be like that described hereinabove.

While a preferred embodiment of the present invention in a ligament anchor system and its use have been shown and described herein, it should be apparent that the present disclosure is made by way of example only and that variations thereto are possible within the scope of the disclosure without departing from the subject matter coming with the scope of the following claims and a reasonable equivalency thereof, which claims we regard as our invention.

We claim:

1. A ligament anchor system comprising, a pair of longitudinally open externally threaded footings; means for turning each said threaded footings into a tapped bone cortex; a pair of stud means, each stud means including a flared end, a body that has a diameter to fit through the longitudinal passage of said threaded footing, and means for maintaining a ligament means thereto, said stud means flared end terminating in a lip wherefrom a lock wall extends to intersect said stud means body, said lip diameter being slightly greater than said threaded footing longitudinal opening wall diameter, which said stud means flared end is cut longitudinally into said stud means body to receive and maintain a ligament means fitted therealong to allow for collapse of said flared end reducing said lip diameter to less than said threaded footing longitudinal opening wall diameter; and ligament means for arrangement between said pair of stud means.

2. A ligament anchor system as recited in claim 1, wherein each threaded footing includes a flat forward end surface to receive the stud flared end lock wall fitting thereover; and the footing longitudinal opening, at a rear end, is walled to form a hexagonal cross-section for receiving a hexagonal end of a shaft fitted therein as the means for turning said threaded footing.

3. A ligament anchor system as recited in claim 2, wherein the threaded footing threads forward face slopes at an angle of from twenty (20) to forty-five (45) degrees to the vertical, and the threads rear face slopes at an angle from zero (0) to thirty (30) degrees to the vertical.

4. A ligament anchor system as recited in claim 3, wherein the footing thread forward face is at an angle of approximately thirty (30) degrees to the vertical and the sleeve thread rear face is at an angle of approximately twelve (12) degrees to the vertical.

5. A ligament anchor system as recited in claim 2, further including, circumferentially internally grooving of the footing longitudinal opening at an intermediate distance back from the footing flat forward end appropriate to accommodate the stud flared end fitted therein.

6. A ligament anchor system as recited in claim 1, wherein the threaded sleeve is formed of a Delrin TM plastic material; and an x-ray marker means is installed in said threaded sleeve.

7. A ligament anchor system as recited in claim 1, wherein the pair of stud means includes an eyelet end that is secured to the end of the stud means body opposite to the stud means flared end.

8. A ligament anchor system as recited in claim 7, wherein the stud means body is cylindrical and the stud means flared end is pie shaped, the greatest diameter face thereof arranged across said stud means cylindrical body; and at least one of the pair of studs cross-cuts extends the length of said stud means cylindrical body and into the eyelet end.

9. A ligament anchor system as recited in claim 8, wherein the cross-cut from the stud means flared end into the stud means eyelet end is at approximately a right angle to opposite parallel faces of said stud means eyelet end.

10. A ligament anchor system as recited in claim 8, wherein the stud means is formed of a resilient material.

11. A ligament anchor system as recited in claim 10, wherein the stud means is formed of a Delrin TM plastic material.

12. A ligament anchor system as recited in claim 1, wherein a ligament of the ligament means is formed into a closed loop.

13. A ligament anchor system as recited in claim 11, further including, as the ligament means, a stint that is formed into a closed loop.

14. A ligament anchor system as recited in claim 1, wherein the stud means are individually secured to extend axially from opposite ends of a prosthetic ligament.

15. A ligament anchor system as recited in claim 1, further including at least a pair of equally spaced notches that are formed in a flat forward end of the threaded footing and extend into the threaded footing exterior threads; and tool means consisting of a rod or tube that includes at least a pair of outwardly extending equally spaced ear or tab means that project longitudinally outwardly from said thin rod or tube end to fit into each of said pair of notches, straddling said threaded footing forward end, the ears or tabs seated below the thread apex of said threaded footing threads.

16. A ligament anchor system as recited in claim 15, wherein the tool means is a straight cylindrical section and the individual ear or tab means each have a thickness that is less than the height of the exterior threads of the threaded footing.

17. A process for installing a cruciate ligament in a knee arthoscopic surgical procedure where a tunnel has been formed between femoral and tibial cortexes through the intra articular joint and ligament origins, and the femoral and tibial cortexes have been tapped, comprising the steps of, turning each of a pair of threaded footings into the femoral and tibial tapped cortexes, said threaded footings each having a longitudinal passage therethrough; mounting ligament means to ends of each of a pair of stud means, said stud means, each having a body that will fit longitudinally through one of the threaded footings, with said ligament means ends attached to ends of each of said stud means cylindrical body, each of which stud means includes, on its other end, an outwardly flared end section that terminates in a lip, which lip has a diameter that is greater than that of said threaded footing longitudinal passage, and which stud means flared end is cross-cut longitudinally into its cylindrical body; and installing each of said pair of stud means flared ends into said threaded footings, each stud means flared end collapsing along said cross-cuts to fit within and pass along said threaded footing longitudinal passage until said stud means flared end lip emerges from and said flared end lip flexes over a threaded footing end thereby locking said stud means in said threaded footing, the ligament means extending therebetween across the intra articular joint.

18. A process as recited in claim 17, wherein each threaded footing longitudinal passage is sided at one end to receive a tool having a like sided end arranged for fitting through a cylindrical portion of said threaded footing longitudinal passage and into said threaded footing; and turning said tool and threaded footing into the tapped cortex ends of the tunnel.

19. A process as recited in claim 18, wherein a first threaded footing is installed in a tapped cortex end of the tunnel and receives a first stud means fitted therein; the second threaded footing is then installed in the other tapped cortex end of the tunnel, and a surgeon operating through an arthoscopic port formed into the patient's knee fits said second stud means into said installed second threaded footing and urges said second stud means therein until said second stub means flared end exits said second threaded footing and said second stud means lip flexes over said threaded footing end.

20. A process as recited in claim 19, further including the steps of, adjusting the tensile stress exerted on the ligament means stretched between said pair of stud means by releasing, at a tapped cortex tunnel end, one of said stud means out of its engagement with a threaded footing as by closing the stud flared end lip segments together to where said flared end lip circumference is less than that of the threaded footing longitudinal passage, releasing said stud means that then slides back along said threaded footing longitudinal passage; and, through the arthoscopic port, reconfiguring the ligament means so as to appropriately lengthen or shorten it.

21. A process as recited in claim 19, further including the steps of, for finely adjusting the tensile stress on the ligament means, turning the threaded footing into or out of said cortex threads at a tunnel end.

22. A process as recited in claim 21, wherein the threaded footing includes at least a pair of equally spaced longitudinal slots that are formed into the exterior threads from a footing end that, when installed, will be proximate to the cortex surface; and, with a tool that is configured to straddle said threaded footing and which tool includes equally spaced ear or tab means that have a lesser thickness than the threaded footing exterior thread height to fit into said longitudinal slots, for turning said threaded footing into or out of said cortex threads.

23. A process as recited in claim 17, wherein the ligament means is a biologic or prosthetic ligament, or a ligament type device, and may include a stint therewith.

* * * * *